(12) United States Patent
Kim et al.

(10) Patent No.: US 8,574,556 B2
(45) Date of Patent: Nov. 5, 2013

(54) **ANTIBACTERIAL PHARMACEUTICAL COMPOSITION COMPRISING *ACERIPHYLLUM ROSSII* EXTRACT AND ACTIVE COMPOUNDS ISOLATED THEREFROM**

(75) Inventors: Won Gon Kim, Daejeon (KR); Chang Ji Zheng, Daejeon (KR); Ki Young Kim, Incheon (KR); Mi Jin Sohn, Daejeon (KP)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 189 days.

(21) Appl. No.: 13/129,087

(22) PCT Filed: Nov. 12, 2008

(86) PCT No.: PCT/KR2008/006654
§ 371 (c)(1),
(2), (4) Date: May 12, 2011

(87) PCT Pub. No.: WO2010/055960
PCT Pub. Date: May 20, 2010

(65) Prior Publication Data
US 2011/0223118 A1    Sep. 15, 2011

(51) Int. Cl.
*A61K 8/365* (2006.01)
*A61K 8/00* (2006.01)
*A61K 8/18* (2006.01)

(52) U.S. Cl.
USPC .............................................. 424/55; 424/58

(58) Field of Classification Search
USPC .................................................... 424/55, 58
See application file for complete search history.

(56) References Cited

FOREIGN PATENT DOCUMENTS

KR    10-0859096 B1    9/2008

OTHER PUBLICATIONS

Pfeltz, et al., The Escalating Challenge of Vancomycin Resistance in *Staphylococcus aureus*. Current Drug Targets-Infectious Disorders, 2004, 4, pp. 273-294.
Levy, et al., Antibacterial resistance worldwide: causes, challenges and responses. Nature Med. 2004, 10, pp. 122-129.
Han et aL, Flavonol Glycosides from the Aerial Parts of *Aceriphyllum rossii* and Their Antioxidant Activities, Arch Pharm Res 27, pp. 390-395, 2004.
Min, et al., Anticomplementary Activity of Triterpenoids from the Whole Plant of *Aceriphyllum rossii* against the Classical Pathway, Planta Medica, V.74, No. 7, pp. 726-729.

*Primary Examiner* — San-Ming Hui
(74) *Attorney, Agent, or Firm* — Chainey P. Singleton; Daniel J. Chalker; Chalker Flores, LLP

(57) ABSTRACT

The present invention relates to an antibacterial pharmaceutical composition comprising an *Aceriphyllum rossii* extract, and aceriphyllic acid A and 3-oxo-12-oleanen-27-oic acid isolated therefrom. The *Aceriphyllum rossii* extract of the present invention, and aceriphyllic acid A and 3-oxo-12-oleanen-27-oic acid isolated therefrom have strong antibacterial activities against *Staphylococcus aureus*, methicillin-resistant *S. aureus*, quinolone-resistant *S. aureus*, *Acinetobacter calcoaceticus*, *Micrococcus luteus*, *Bacillus subtilis* or *Streptococcus mutans*, *Propionibacterium acnes*, thereby being used for the prevention or treatment of pathogenic bacterial and resistant bacterial infections, cariogenic bacterial and acne bacterial infections.

10 Claims, No Drawings

ANTIBACTERIAL PHARMACEUTICAL COMPOSITION COMPRISING *ACERIPHYLLUM ROSSII* EXTRACT AND ACTIVE COMPOUNDS ISOLATED THEREFROM

TECHNICAL FIELD

The present invention relates to an antibacterial pharmaceutical composition comprising an *Aceriphyllum rossii* extract and active compounds isolated therefrom.

BACKGROUND ART

Pathogenic microorganisms directly or indirectly cause a variety of economic, environmental, and medical problems: loss due to spoilage during product distribution in the food industries, harmful effects of excessive pesticide use on human health and the environment in the agricultural industries, and emergence of resistant strains due to misuse or abuse of antibiotics.

Since the first case of vancomycin-resistant *staphylococcus aureus* (VRSA), which has high-level resistance to vancomycin, the antibiotic of last resort for use against infection with common *S. aureus* strains, was reported by the Centers for Disease Control in 2002, there has been considerable concern about the spread of so-called super bacteria. Methicillin-resistant *s. aureus* (MRSA), which is susceptible only to vancomycin, has caused great concern since 1970, and vancomycin-resistant *enterococcus* (VRE) showing resistance to vancomycin was first isolated in Europe in 1988. In the late 1990's, the appearance of vancomycin intermediate-resistant *s. aureus* (VISA) was reported in Japan, the U.S.A., France, and Korea. The emergence of these antibiotic-resistant bacteria has now become a worldwide problem, and thus there is an urgent need for the development of new antibiotics (Pfeltz, R. F. and Wilkinson, B. J. 2004. The escalating challenge of vancomycin resistance in *Staphylococcus aureus*. *Drug targets-infect. Disord.* 4: 273-294.; Levy, S. B. and Marshall, B. 2004. Antibacterial resistance worldwide: causes, challenges and responses. *Nature Med.* 10: 122-129.).

Most of the currently used antibiotics are prepared by chemical synthesis, which has many limitations including high costs and the occurrence of side effects. Therefore, recent studies have been actively made to isolate new antimicrobial substances from natural sources. In this regard, it has to be considered whether the antimicrobial substances isolated from natural sources have a broad antimicrobial spectrum and are safe for long-term use without the possibility of side effects.

Meanwhile, oral diseases are generally caused by various kinds of bacteria in the mouth, which can be divided into cariogenic bacteria and periodontopathic bacteria, represented by *S. mutans* and *P. gingivalis*, respectively. Several disinfectants have been used in dental care products in order to remove oral bacteria. Examples of the disinfectants used in dental care products include raw materials such as cetylpyridinium chloride, hexylkonium chloride, benzalkonium chloride, dequalinium chloride, chlorhexidine, triclosan, thymol, isopropyl methylphenol, and alkyldiaminoethylglycine hydrochloride, polyphenols isolated from natural products, and silver compounds. In recent years, there has been an increasing interest in the use of natural extracts, and thus many studies have been conducted on a variety of plants, of which effects on oral diseases have been also known. Accordingly, plant extracts have been used in numerous oral compositions for the prevention of oral diseases.

Acne is a common skin disease that induces inflammation at the skin surface of the face, neck, chest or back. Acne develops mostly in young people due to several factors, including hormonal imbalance, bacterial infection, stress, food, or cosmetic application. Especially, *Propionibacterium acnes*, which is one of major organisms isolated from the surface of skin, induces an inflammation in the sebaceous glands or hair pores. *P. acnes* secretes lipase and degrades sebum oils into free fatty acids, which are potent acne stimuli. These free fatty acids stimulate the hair follicle, and form a comedo which is the first step of forming an acne lesion. Comedo refers to a sebum sac formed by outlet obstruction of the sebaceous glands. These bacteria also secrete leukocyte chemotatic factors, thereby infiltrating leukocytes into the hair follicle. These leukocytes stimulate and destroy the hair follicle wall. Therefore, *P. acnes* is considered to play an important role in acne development by secreting inflammation-inducing factors. As therapeutic agents for acne, antibiotics are usually employed to inhibit inflammation or kill the bacteria. For example, triclosan, benzyl peroxide, azelaic acid, retinoid, tetracycline, erythromycin, macrolide and clindamycin are among these antibiotics. However, these antibiotics have been known to induce side effects. Benzyl peroxide and retinoid bring about xerosis cutis and skin irritation if they are used excessively as treatments, and several reports also suggest that in the case of tetracycline, erythromycin, macrolide and clindamycin, there are several side effects such as appearance of resistant bacteria, organ damage, and immunohypersensitivity if they have been taken for a long time. In addition, triclosan is converted into an environmental hormone when exposed to light, inducing severe environmental pollution. Therefore, there is a need for substances which have no side effects and exhibit a strong antibacterial activity.

Meanwhile, *Aceriphyllum rossii* is a perennial herb with a height of 10-30 cm, which belongs to the family Saxifragaceae of the order Rosales of the class Dicotyledoneae, and also called Mukdenia or Saxifraga. The leaves of *Aceriphyllum rossii* resemble maple leaves, and it can be grown in a rock garden, and thus is also called a rock maple. The flower and palm-like leaves of *Aceriphyllum rossii* have 5-7 deeply divided, serrated lobes, and their surfaces are glossy. Young leaves, in particular, are used for food. Since *Aceriphyllum rossii* has cardiotonic and diuretic effects, 10-15 g of *Aceriphyllum rossii* may be extracted with boiling water, and taken to treat palpitation and urinary disorder. As a home remedy, the roots may serve as a substitute for Acorns gramineus. *Aceriphyllum rossii* includes the active ingredients of triterpenes and flavonoids. It has been reported that triterpenes have cytotoxicity against cancer cells (K562, HL-60) and ACAT inhibitory activity, and flavonoids show antioxidant activity (Han et al., Arch Pharm Res 27:390-395, 2004).

As described above, various pharmacological activities of *Aceriphyllum rossii* have been reported, but there has been no report on the antibacterial activity of *Aceriphyllum rossii*.

DISCLOSURE

Technical Problem

Accordingly, in order to explore new antimicrobial substances in plants, the present inventors have made an effort to screen substances having inhibitory effects on microbial growth from 2,000 kinds of plant extracts. They found that an *Aceriphyllum rossii* extract and active ingredients isolated therefrom have strong antibacterial activities against pathogenic bacteria, resistant bacteria, cariogenic bacteria, and acne bacteria, thereby completing the present invention.

Technical Solution

It is an object of the present invention to provide an antibacterial pharmaceutical composition comprising an *Aceriphyllum rossii* extract and active ingredients isolated therefrom.

It is another object of the present invention to provide an antibacterial oral composition comprising an *Aceriphyllum rossii* extract and active ingredients isolated therefrom.

It is still another object of the present invention to provide an anti-acne composition and a cosmetic composition for alleviating acne, comprising an *Aceriphyllum rossii* extract and active ingredients isolated therefrom.

BEST MODE FOR CARRYING OUT THE INVENTION

The present invention provides an antibacterial pharmaceutical composition comprising an *Aceriphyllum rossii* extract and active ingredients isolated therefrom.

Hereinafter, the present invention will be described in detail.

The *Aceriphyllum rossii* extract according to the present invention and the active ingredients isolated therefrom are extracted and isolated by the following method.

Dried roots of *Aceriphyllum rossii* are added to an organic solvent such as methanol, and stirred to extract active ingredients. Then, the ingredients are concentrated under reduced pressure, and the organic solvent is removed to obtain a methanol extract of *Aceriphyllum rossii* root. The methanol extract of *Aceriphyllum rossii* root is subjected to solvent extraction with ethyl acetate, and the ethyl acetate layer is concentrated under reduced pressure and freeze-dried to obtain an ethyl acetate extract of *Aceriphyllum rossii* root in a powder form. The ethyl acetate extract of *Aceriphyllum rossii* root is subjected to silica gel column thin layer chromatography using a solvent of chloroform:methanol (10:1) to obtain active fractions. The active fractions are further subjected to silica gel column thin layer chromatography using a solvent of chloroform:methanol (30:1) to obtain pure compounds 1 and 2. Compounds 1 and 2 were identified as aceriphyllic acid A and 3-oxo-12-oleanen-27-oic acid, respectively.

The aceriphyllic acid A and 3-oxo-12-oleanen-27-oic acid may be used in the form of a pharmaceutically acceptable salt, and may include any salt, ester derivative, hydrate, and solvate prepared by the conventional method in the related art. As the salt, acid addition salts produced with pharmaceutically acceptable free acids are preferred. As the free acids, organic acids and inorganic acids may be used. Examples of the inorganic acids may include hydrochloric acid, bromic acid, sulfuric acid, and phosphoric acid, and examples of the organic acids may include citric acid, acetic acid, lactic acid, maleic acid, fumaric acid, gluconic acid, methane sulfonic acid, glycolic acid, succinic acid, 4-toluene sulfonic acid, trifluoroacetic acid, galacturonic acid, embonic acid, glutamic acid, and aspartic acid.

The aceriphyllic acid A and 3-oxo-12-oleanen-27-oic acid of the present invention may be prepared from natural medicinal herbs, for example, extracted and isolated from *Aceriphyllum rossii*. However, it may also be synthesized by chemical methods, or a commercially available drug may be used.

The *Aceriphyllum rossii* extract according to the present invention and aceriphyllic acid A and 3-oxo-12-oleanen-27-oic acid isolated therefrom exhibit strong antibacterial activities against *Staphylococcus aureus*, methicillin-resistant *S. aureus*, quinolone-resistant *S. aureus*, *Acinetobacter calcoaceticus*, *Micrococcus luteus*, *Bacillus subtilis* or *Streptococcus mutans*, and *Propionibacterium acnes*. Therefore, the *Aceriphyllum rossii* extract according to the present invention and aceriphyllic acid A and 3-oxo-12-oleanen-27-oic acid isolated therefrom can be used for the prevention or treatment of pathogenic bacterial and resistant bacterial infections, and cariogenic bacterial and acne bacterial infections.

The pharmaceutical composition of the present invention may further include one or more of the known active ingredients that have antibacterial activities against pathogenic bacteria and resistant bacteria, together with the *Aceriphyllum rossii* extract and aceriphyllic acid A and 3-oxo-12-oleanen-27-oic acid isolated therefrom.

For administration, the pharmaceutical composition of the present invention may further include pharmaceutically acceptable carriers, excipients, or diluents, in addition to the above described active ingredients. Examples of the carriers, excipients, and diluents may include lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil.

According to conventional methods, the pharmaceutical composition of the present invention may be formulated into an oral preparation such as a powder, a granule, a tablet, a capsule, a suspension, an emulsion, a syrup, and an aerosol, an external preparation, suppository, or a sterilized injectable solution. In detail, such preparations may be prepared using diluents or excipients ordinarily employed, such as a filler, an extender, a binder, a wetting agent, a disintegrating agent, and a surfactant. Examples of the solid preparation for oral administration include a tablet, a pill, a powder, a granule, and a capsule, but are not limited thereto. The solid preparation may be prepared by mixing the *Aceriphyllum rossii* extract and the aceriphyllic acid A and 3-oxo-12-oleanen-27-oic acid isolated therefrom with at least one excipient such as starch, calcium carbonate, sucrose, lactose, and gelatin. Further, in addition to the excipients, lubricants such as magnesium stearate and talc may be used. Examples of a liquid preparation for oral administration include a suspension, a liquid for internal use, an emulsion, and a syrup, but are not limited thereto. Various excipients such as a wetting agent, a sweetener, a flavor, and a preservative may be contained, in addition to general diluents such as water and liquid paraffin. Examples of the preparation for parenteral administration include an aseptic aqueous solution, a non-aqueous solvent, a suspension, an emulsion, a lyophilized agent, and suppository. As the non-aqueous solvent and suspension, propylene glycol, polyethylene glycol, plant oil such as olive oil, injectable ester such as ethyloleate may be used. As a suppository base, witepsol, macrogol, tween 61, cacao butter, lauric butter, glycerogelatin or the like may be used.

The pharmaceutical composition of the present invention may be administered orally or parenterally (for example, intravenous, subcutaneous, intraperitoneal, or topical application) depending on its purpose. The dosage of the pharmaceutical composition can vary depending on various factors, including a patient's health condition and weight, disease severity, the kind of formulation, administration route, and administration time, but can be readily selected by those skilled in the art. The *Aceriphyllum rossii* extract and aceriphyllic acid A and 3-oxo-12-oleanen-27-oic acid isolated therefrom can be administered at a daily dosage of 1 mg/kg to 0.5 g/kg, and preferably 10 mg/kg to 0.05 g/kg, one time or several times.

The pharmaceutical composition of the present invention may be used alone or in combination with surgical operations, hormone therapies, chemical therapies, and other methods using biological reaction regulators, in order to prevent or treat pathogenic bacterial and resistant bacterial infections.

The formulation for the oral composition of the present invention is not particularly limited, and it may be specifically formulated into toothpastes, mouthwashes, rinses or the like. In particular, a toothpaste may contain additives such as abrasives, wetting agents, foaming agents, binders, sweeteners, pH regulators, preservatives, other active ingredients, flavors, brightening agents, coloring agents, solvents or the like. Examples of the abrasive additives include calcium carbonate, precipitated silica, aluminum hydroxide, calcium monohydrogen phosphate, and insoluble sodium metaphosphate. Examples of the wetting agent include glycerine, a sorbitol solution, polyethylene glycol, and propylene glycol, and they may be used alone, or in a combination of two or more thereof. Examples of the foaming agent include non-ionic surfactants such as polyoxyethylene sorbitan fatty acid ester, polyoxyethylene (hardened) castor oil, glycerin fatty acid ester, sorbitan fatty acid ester, sucrose fatty acid ester, alkylolamido, and alkylglucoside, and cationic surfactant such as N-alkyldiaminoethylglycin, and the foaming agent is used alone or in combination of two or more thereof. Examples of the binder include hydroxyethylcellulose, hydroxypropylcellulose, xanthan gum, carrageenan, and sodium alginate. Examples of the sweetener include saccharine sodium, aspartame, stevio side, xylitol, and glycyrrhetinic acid. The sweetener is used alone or in combination of two or more thereof. Examples of the pH-control agent include sodium phosphate, disodium phosphate, sodium pyrophosphate, sodium citrate, citric acid, and tartaric acid. Examples of the preservative include paraoxybenzoic acid methyl, paraoxybenzoic acid propyl, and sodium benzoate, and the preservative is used alone or in combination of two or more thereof. Examples of the active ingredient include sodium fluoride, sodium monofluorophosphate, stannous fluoride, chlorohexidine, allantoinchlorohydroxyaluminate, aminocaproic acid, triclosan, cetylpyridinium chloride, zinc chloride, pyridoxine hydrochloride, and tocopherol acetate, and the active ingredient is used alone or in a combination of two or more thereof. Examples of the flavor include peppermint oil, spearmint oil, menthol, and anethole, and suitable amounts of the flavors may be blended. Titanium oxide is blended as the brightening agent, and a food color is blended as the coloring agent. Purified water or ethanol is blended as the solvent.

The cosmetic composition of the present invention may be formulated into a natural cosmetic product-added composition and an acne skin care product by adding a water-soluble skin toner, a viscosity and hardness modifier, a UV absorber, a pigment, a moisturizer, and a preservative, together with the *Aceriphyllum rossii* extract.

Mode for Invention

Hereinafter, the preferred Examples are provided for better understanding. However, these Examples are for illustrative purposes only, and the invention is not intended to be limited thereby.

EXAMPLE 1

Preparation of Root Extract of Aceriphyllum Rossii 2 kg of dried roots of *Aceriphyllum rossii* were added to 4 kg of methanol, and extracted by stirring for 3 hrs. The liquid extract was filtered, and concentrated under reduced pressure to obtain a methanol extract of *Aceriphyllum rossii* root. 500 g of ethyl acetate was added to the methanol extract of *Aceriphyllum rossii* root, and subjected to solvent extraction for 1 hr. The liquid extract was filtered, concentrated under reduced pressure, and freeze-dried to obtain an ethyl acetate extract of *Aceriphyllum rossii* root in a powder form.

EXAMPLE 2

Isolation of Active Ingredients from *Aceriphyllum rossii* Root Extract

The ethyl acetate extract of *Aceriphyllum rossii* root obtained in Example 1 was subjected to silica gel column thin layer chromatography using a solvent of chloroform:methanol (10:1) to obtain active fractions. The active fractions were subjected to silica gel column thin layer chromatography using a solvent of chloroform:methanol (30:1), so as to obtain pure compounds 1 and 2. The compounds 1 and 2 were identified as aceriphyllic acid A and 3-oxo-12-oleanen-27-oic acid by measuring their appearance, molecular weight, molecular formula, polarization degree, and $^{13}$C-NMR spectrum.

<Compound 1> Aceriphyllic Acid A

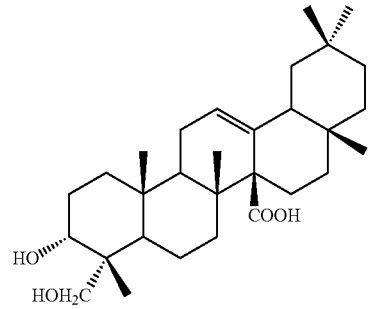

1) Appearance: white powder,
2) Molecular weight: 472,
3) Molecular Formula: $C_{30}H_{48}O_4$,
4) Optical rotation ($[\alpha]_D$): 84.4 (c 1.09, CHCl$_3$),
5) $^{13}$C-NMR (75 MHz, CDCl$_3$): 36.68 (C-1), 26.05 (C-2), 75.81 (C-3), 40.15 (C-4), 46.72 (C-5), 18.08 (C-6), 33.0 (C-7), 35.97 (C-8), 49.47 (C-9), 39.65 (C-10), 22.91 (C-11), 124.42 (C-12), 139.86 (C-13), 57.03 (C-14), 22.41 (C-15), 28.10 (C-16), 31.00 (C-17), 42.13 (C-18), 44.21 (C-19), 33.4 (C-20), 34.29 (C-21), 36.82 (C-22), 70.24 (C-23), 18.08 (C-24), 16.45 (C-25), 18.35 (C-26), 181.3 (C-27), 28.44 (C-28), 33.21 (C-29), 24.01 (C-30).

<Compound 2> 3-Oxo-12-oleanen-27-oic acid

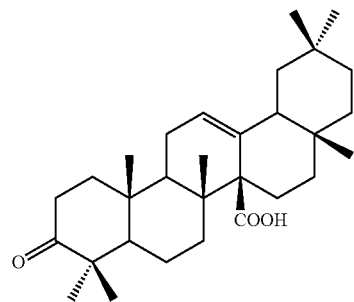

1) Appearance: white powder,
2) Molecular weight: 454,
3) Molecular formula: $C_{30}H_{46}O_3$,
4) Optical rotation ($[\alpha]_D$): 106.42 (c 1.09, $CHCl_3$),
5) $^{13}$C-NMR (75 MHz, $CDCl_3$): 39.2 (C-1), 34.2 (C-2), 218.1 (C-3), 47.1 (C-4), 54.7 (C-5), 19.8 (C-6), 36.1 (C-7), 40.0 (C-8), 46.3 (C-9), 36.9 (C-10), 23.1 (C-11), 125.7 (C-12), 138.2 (C-13), 56.1 (C-14), 22.8 (C-15), 27.9 (C-16), 33.0 (C-17), 49.4 (C-18), 44.4 (C-19), 31.3 (C-20), 34.0 (C-21), 36.7 (C-22), 21.6 (C-23), 27.3 (C-24), 16.5 (C-25), 18.1 (C-26), 181.0 (C-27), 28.5 (C-28), 33.9 (C-29), 23.8 (C-30).

COMPARATIVE EXAMPLE 1

Preparation of Aerial Part Extract of *Aceriphyllum Rossii*

The aerial parts of dried *Aceriphyllum rossii* were extracted in the same manner as in Example 1, so as to obtain an aerial part extract of *Aceriphyllum rossii*.

EXPERIMENTAL EXAMPLE 1

Antibacterial activity of *Aceriphyllum rossii* extract and active ingredients isolated therefrom In order to determine antibacterial activities of the *Aceriphyllum rossii* extract of the present invention and the active ingredients isolated therefrom, the following experiment was performed.

Test strains were cultured in a Mueller Hinton broth, and the antibacterial activities were determined by a broth microdilution assay. The test strains were grown to the mid-logarithmic phase, and diluted to a concentration of $10^5$/ml with the same broth. 0.2 ml of the cells was added to each well of 96-well plates. The samples prepared in Examples 1 and 2 and Comparative Example 1 were serially diluted 2-fold, and added to the plates. The cells were incubated at 30° C. for 18 hrs, and cell growth was measured at 650 nm. MIC was defined as the lowest concentration of the compound that completely inhibits the initiation of cell growth.

*Propionibacterium acnes* was cultured in RCMI liquid media under anaerobic conditions, and the antibacterial activities were determined by a broth microdilution assay. The test strain was pre-cultured in liquid media at 37° C. for 1 to 2 days. 15 μl of test material dissolved in DMSO was added to 3 ml of broth to a concentration of 32 ppm. The sample was serially diluted 2-fold to prepare seven samples with different concentrations. The samples were added to the pre-cultured broth to a microbial concentration of $10^{5-6}$ cfu/ml, and cultured for 1-3 days, followed by measurement of cell growth.

The antibacterial activity of *Aceriphyllum rossii* extract was determined with respect to *Staphylococcus aureus*, and the antibacterial activities of aceriphyllic acid A and 3-oxo-12-oleanen-27-oic acid were determined with respect to 15 different types of strains. Triclosan, oxacillin, and norfloxacin, which are commercially available antibiotics, were used for comparison.

The antibacterial activities of *Aceriphyllum rossii* extract were shown in Table 1, and those of *Aceriphyllum rossii* extract, aceriphyllic acid A, and 3-oxo-12-oleanen-27-oic acid were shown in Table 2.

TABLE 1

Antibacterial activity of *Aceriphyllum rossii* extract against *Staphylococcus aureus*

| | Antibacterial activity (%) | |
|---|---|---|
| MIC (μg/ml) | Aerial part extract of *Aceriphyllum rossii* | Root extract of *Aceriphyllum rossi* |
| 200 | 100 | 100 |
| 100 | 74 | 100 |
| 50 | 55 | 100 |
| 25 | 46 | 100 |
| 12.5 | — | 100 |
| 6.25 | — | 100 |
| 3.125 | — | 45 |

As shown in Table 1, MIC of the aerial part extract of *Aceriphyllum rossii* against *Staphylococcus aureus* was 200 μg/ml, whereas MIC of the root extract of *Aceriphyllum rossii* against *Staphylococcus aureus* was 6.25 μg/ml, showing 32-fold stronger activity than that of the aerial part extract of *Aceriphyllum rossii*. In addition, the aerial part extract of *Aceriphyllum rossii* and the root extract of *Aceriphyllum rossii* also exhibited antibacterial activities against methicillin-resistant *S. aureus* and quinolone-resistant *S. aureus*, which are similar to those against *Staphylococcus aureus*.

TABLE 2

Antibacterial activities of *Aceriphyllum rossii* extract, aceriphyllic acid A, and 3-oxo-12-oleanen-27-oic acid

| | MIC (μg/Ml) | | | | | |
|---|---|---|---|---|---|---|
| Strain | Extract | Aceriphyllic acid A | 3-Oxo-12-oleanen-27-oic acid | Triclosan | Oxacillin | Norfloxacin |
| *Staphylococcus aureus* 503 | 4 | 2 | 2 | 0.006 | 0.25 | 1 |
| *Staphylococcus aureus* KCTC1916 | 8 | 4 | 2 | 0.006 | 0.25 | 0.25 |
| *Staphylococcus aureus* RN4220 | 8 | 4 | 4 | 0.006 | 0.25 | 1 |
| *Staphylococcus aureus* CCARM3167(MRSA) | 8 | 4 | 4 | 0.006 | 500 | 8 |
| *Staphylococcus aureus* CCARM3506(MRSA) | 8 | 4 | 8 | 0.006 | 500 | 1 |
| *Staphylococcus aureus* CCARM3505(QRSA) | 16 | 4 | 8 | 0.006 | 0.5 | 250 |
| *Staphylococcus aureus* CCARM3519(QRSA) | 16 | 4 | 8 | 0.006 | 0.5 | 125 |
| *Bacillus subtilis* KCTC1021 | 8 | 1 | 2 | 0.003 | 0.25 | 0.25 |
| *Acinetobacter calcoaceticus* KCTC2357 | 4 | 2 | 2 | 0.003 | 0.125 | 0.25 |
| *Micrococcus luteus* KCTC1056 | 8 | 2 | 2 | 1 | 8 | 2 |
| *Streptococcus pneumoniae* KCTC3932 | >64 | 32 | 16 | 32 | 2 | 2 |
| *Enterococcus faecium* KCTC3122 | 16 | 8 | >64 | 4 | 2 | 8 |
| *Streptococcus mutans* KCTC5248 | 8 | 2 | 4 | 1 | 0.06 | 8 |
| *Streptococcus mutans* KCTC3065 | 8 | 2 | 4 | 1 | 0.06 | 8 |

TABLE 2-continued

Antibacterial activities of *Aceriphyllum rossii* extract, aceriphyllic acid A, and 3-oxo-12-oleanen-27-oic acid

| | MIC (μg/Ml) | | | | | |
|---|---|---|---|---|---|---|
| Strain | Extract | Aceriphyllic acid A | 3-Oxo-12-oleanen-27-oic acid | Triclosan | Oxacillin | Norfloxacin |
| *Streptococcus mutans* KCTC3289 | 8 | 4 | 4 | 1 | 0.06 | 8 |
| *Propionibacterium acnes* ATCC6919 | 4-8 | 2 | 2 | — | — | — |

As shown in Table 2, the *Aceriphyllum rossii* extract showed MIC of 4-16 μg/ml against *Staphylococcus aureus*, methicillin-resistant *S. aureus*, and quinolone-resistant *S. aureus*. Aceriphyllic acid A showed MIC of 2-4 μg/ml against *Staphylococcus aureus*, methicillin-resistant *S. aureus*, and quinolone-resistant *S. aureus*, indicating its strong antibacterial activity.

3-Oxo-12-oleanen-27-oic acid showed MIC of 2-8 μg/ml against *Staphylococcus aureus*, methicillin-resistant *S. aureus*, and quinolone-resistant *S. aureus*, which is similar to or slightly weaker than that of aceriphyllic acid A. In addition, aceriphyllic acid A and 3-oxo-12-oleanen-27-oic acid showed MIC of 1-2 μg/ml against *Acinetobacter calcoaceticus, Micrococcus luteus*, and *Bacillus subtilis*.

Further, the *Aceriphyllum rossii* extract, aceriphyllic acid A, and 3-oxo-12-oleanen-27-oic acid showed strong antibacterial activities against cariogenic bacteria (*Streptococcus mutans*). Each of the *Aceriphyllum rossii* extract, aceriphyllic acid A, and 3-oxo-12-oleanen-27-oic acid showed MIC of 8 μg/ml, 2-4 μg/ml, and 4 μg/ml, indicating their strong antibacterial activities against cariogenic bacteria.

Furthermore, the *Aceriphyllum rossii* extract, aceriphyllic acid A, and 3-oxo-12-oleanen-27-oic acid showed strong antibacterial activities against acne bacteria (*Propionibacterium acnes*). Each of the *Aceriphyllum rossii* extract, aceriphyllic acid A, and 3-oxo-12-oleanen-27-oic acid showed MIC of 8 μg/ml, 2 μg/ml, and 2 μg/ml, indicating their strong antibacterial activities against acne bacteria.

Accordingly, it can be seen that the *Aceriphyllum rossii* extract of the present invention, and aceriphyllic acid A and 3-oxo-12-oleanen-27-oic acid isolated therefrom, have strong antibacterial activities against microorganisms including cariogenic bacteria and acne bacteria.

Hereinbelow, Preparation Examples for the composition of the present invention will be described.

PREPARATION EXAMPLE 1

Preparation of Powder

*Aceriphyllum rossii* extract (or aceriphyllic acid A or 3-oxo-12-oleanen-27-oic acid) 0.1 g
Lactose 1.5 g
Talc 0.5 g
The ingredients were mixed and filled in an airtight sac to prepare a powder agent.

PREPARATION EXAMPLE 2

Preparation of Tablet

*Aceriphyllum rossii* extract (or aceriphyllic acid A or 3-oxo-12-oleanen-27-oic acid) 0.1 g
Lactose 7.9 g
Crystalline cellulose 1.5 g
Magnesium Stearate 0.5 g
The ingredients were mixed and prepared into a tablet using a direct tabletting method.

PREPARATION EXAMPLE 3

Preparation of Capsule

*Aceriphyllum rossii* extract (or aceriphyllic acid A or 3-oxo-12-oleanen-27-oic acid) 0.1 g
Corn starch 5 g
Carboxy cellulose 4.9 g
The ingredients were mixed to prepare a powder, and then the powder was filled into a gelatin capsule according to a typical procedure to provide a capsule.

PREPARATION EXAMPLE 4

Preparation of Injectable Formulation

*Aceriphyllum rossii* extract (or aceriphyllic acid A or 3-oxo-12-oleanen-27-oic acid) 0.1 g
Sterile distilled water, proper amount
pH adjuster, proper amount
According to a typical procedure, an injectable formulation comprising the above ingredients was prepared into a (2 ml) ampule.

PREPARATION EXAMPLE 5

Preparation of Liquid Formulation

*Aceriphyllum rossii* extract (or aceriphyllic acid A or 3-oxo-12-oleanen-27-oic acid) 0.1 g
High fructose corn syrup 10 g
Mannitol 5 g
Purified water, proper amount
According to a typical procedure, each ingredient was solubilized in purified water. A proper amount of lemon flavor was added to the above ingredients, and it was mixed. Then, purified water was added to a volume of 100 ml, poured into a brown bottle, and sterilized to prepare a liquid formulation.

INDUSTRIAL APPLICABILITY

The *Aceriphyllum rossii* extract of the present invention, and aceriphyllic acid A and 3-oxo-12-oleanen-27-oic acid isolated therefrom have strong antibacterial activities against

*Staphylococcus aureus*, methicillin-resistant *S. aureus*, quinolone-resistant *S. aureus*, *Acinetobacter calcoaceticus*, *Micrococcus luteus*, *Bacillus subtilis* or *Streptococcus mutans*, *Propionibacterium acnes*. Accordingly, the *Aceriphyllum rossii* extract of the present invention, and aceriphyllic acid A and 3-oxo-12-oleanen-27-oic acid isolated therefrom can be used for the prevention or treatment of pathogenic bacterial and resistant bacterial infections, cariogenic bacterial and acne bacterial infections.

What is claimed is:

1. A method of treating a bacterial infection in a subject in need of such treatment, the method comprising administering to the subject a composition comprising an effective amount of an *Aceriphyllum rossii* extract, wherein the bacterial infection is caused by one or more microorganisms selected from the group consisting of *Staphylococcus aureus*, methicillin-resistant *S. aureus*, quinolone-resistant *S. aureus*, *Acinetobacter calcoaceticus*, *Micrococcus luteus*, *Bacillus subtilis*, *Streptococcus mutans*, and *Propionibacterium acnes*.

2. The method according to claim 1, wherein the *Aceriphyllum rossii* extract comprises a root extract of *Aceriphyllum rossii*.

3. The method according to claim 1, wherein the bacterial infection is a cariogenic bacterial infection.

4. The method according to claim 1, wherein the bacterial infection is an acne bacterial infection.

5. A method of treating a bacterial infection in a subject in need of such treatment, the method comprising administering to the subject a composition comprising an effective amount of aceriphyllic acid A or 3-oxo-12-oleanen-27-oic acid, wherein the bacterial infection is caused by one or more microorganisms selected from the group consisting of *Staphylococcus aureus*, methicillin-resistant *S. aureus*, quinolone-resistant *S. aureus*, *Acinetobacter calcoaceticus*, *Micrococcus luteus*, *Bacillus subtilis*, *Streptococcus mutans*, and *Propionibacterium acnes*.

6. The method according to claim 5, wherein the aceriphyllic acid A or 3-oxo12-oleanen-27-oic acid is a root extract of *Aceriphyllum rossii*.

7. The method according to claim 5, wherein the bacterial infection is a cariogenic bacterial infection.

8. The method according to claim 5, wherein the bacterial infection is an acne bacterial infection.

9. A method of treating a cariogenic bacterial infection in a subject in need of such treatment, the method comprising contacting an oral surface with an oral hygiene product comprising an effective amount of at least one substance selected from the group consisting of an *Aceriphyllum rossii* extract, aceriphyllic acid A and 3-oxo-12-oleanen-27-oic acid, wherein the cariogenic bacterial infection is caused by *Streptococcus mutans*.

10. The method according to claim 9, wherein the oral hygiene product is toothpaste or mouth-washing liquid.

* * * * *